US012690765B2

(12) United States Patent
Yukimori et al.

(10) Patent No.: US 12,690,765 B2
(45) Date of Patent: Jul. 28, 2026

(54) OPHTHALMOLOGIC APPARATUS

(71) Applicant: TOPCON CORPORATION, Tokyo (JP)

(72) Inventors: Takafumi Yukimori, Tokyo (JP); Makoto Saika, Tokyo (JP); Yoko Tatara, Tokyo (JP); Akio Hayashi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 453 days.

(21) Appl. No.: 18/126,445

(22) Filed: Mar. 26, 2023

(65) Prior Publication Data

US 2023/0309814 A1 Oct. 5, 2023

(30) Foreign Application Priority Data

Mar. 29, 2022 (JP) ................................. 2022-053982

(51) Int. Cl.
*A61B 3/00* (2006.01)
*A61B 3/103* (2006.01)
(52) U.S. Cl.
CPC .......... *A61B 3/0091* (2013.01); *A61B 3/0058* (2013.01); *A61B 3/1035* (2013.01)
(58) Field of Classification Search
CPC ... A61B 3/0091; A61B 3/0058; A61B 3/1035; A61B 3/022; A61B 3/024; A61B 3/028; A61B 3/1005; A61B 3/102; A61B 3/103; A61B 3/12; A61B 3/032; A61B 3/10
See application file for complete search history.

(56) References Cited

U.S. PATENT DOCUMENTS

| | | | |
|---|---|---|---|
| 5,777,718 A | 7/1998 | Kohayakawa | |
| 5,844,661 A | 12/1998 | Uchida | |
| 5,859,688 A | 1/1999 | Hosoi | |
| 5,929,971 A | 7/1999 | Hosoi | |

(Continued)

FOREIGN PATENT DOCUMENTS

| | | |
|---|---|---|
| CN | 113208884 A | 8/2021 |
| EP | 3175776 A1 | 7/2017 |

(Continued)

OTHER PUBLICATIONS

Horino, JP 2017099640 A, Jun. 8, 2017, Espacenet Machine Translation (Year: 2017).*

(Continued)

*Primary Examiner* — Balram T Parbadia
*Assistant Examiner* — Ray Alexander Dean
(74) *Attorney, Agent, or Firm* — Tucker Ellis LLP

(57) ABSTRACT

An ophthalmologic apparatus includes an objective measurement optical system that is configured to objectively measure eye characteristics of a subject eye; an optotype projection system that is configured to present a fixation target to the subject eye at a predetermined presentation position and apply fog to the subject eye; and a controller that is configured to control the objective measurement optical system and optotype projection system. The controller is further configured to objectively measure the eye characteristics over time by changing a presentation position of the fixation target from the predetermined presentation position in a direction to increase an amount of fog and presenting the fixation target.

24 Claims, 6 Drawing Sheets

(56) References Cited

U.S. PATENT DOCUMENTS

| | | | |
|---|---|---|---|
| 5,956,121 | A | 9/1999 | Hosoi |
| 2005/0018132 | A1 | 1/2005 | Fukuma |
| 2005/0264760 | A1 | 12/2005 | Ikezawa |
| 2009/0303439 | A1 | 12/2009 | Kawai |
| 2011/0228225 | A1 | 9/2011 | Liang |
| 2013/0208244 | A1* | 8/2013 | Sakagawa .............. A61B 3/103 |
| | | | 351/205 |
| 2018/0064339 | A1 | 3/2018 | Takii et al. |
| 2019/0099073 | A1* | 4/2019 | Takii .................... A61B 3/0041 |
| 2022/0095910 | A1 | 3/2022 | Horino et al. |

FOREIGN PATENT DOCUMENTS

| | | | | |
|---|---|---|---|---|
| GB | 2355540 | A | | 4/2001 |
| JP | H06197868 | A | | 7/1994 |
| JP | H06233741 | A | | 8/1994 |
| JP | H0910175 | A | | 1/1997 |
| JP | H0994223 | A | | 4/1997 |
| JP | H11113848 | A | | 4/1999 |
| JP | H11346997 | A | | 12/1999 |
| JP | 4330399 | B2 | | 9/2009 |
| JP | 2010082252 | A | | 4/2010 |
| JP | 2015029527 | A | | 2/2015 |
| JP | 2017099640 | A | * 6/2017 | ............ A61B 3/032 |
| JP | 2018038788 | A | | 3/2018 |
| JP | 2018042760 | A | | 3/2018 |
| JP | 2018143585 | A | | 9/2018 |
| JP | 2020031827 | A | * 3/2020 | |
| JP | 6733160 | B2 | | 7/2020 |
| JP | 6828234 | B | | 2/2021 |
| JP | 2021065669 | A | | 4/2021 |
| WO | 2021049314 | A1 | | 3/2021 |

OTHER PUBLICATIONS

Tatara, JP 2020031827 A, Mar. 5, 2020, Espacenet Machine Translation (Year: 2020).*

European Search Report from corresponding European Application No. 23164359.4 mailed on Aug. 1, 2023, 10 pages.

Carlo Aleci et al.: "The optokinetic response is effective to assess obje ctive visual acuity in patients with cataract and age related macular degeneration"; Int Ophthalmol, Published on Aug. 14, 2018, 10 pages.

European Search Report from corresponding European Application No. EP23164349, mailed on Jul. 28, 2023, 7 pages.

European Search Report from corresponding European Application No. 23164371, mailed on Aug. 1, 2023, 7 pages.

Japanese Office Action from corresponding Application No. 2022-053984 mailed on Nov. 25, 2025, 6 pages with translation.

Japanese Office Action from corresponding Application No. 2022-053982 mailed on Nov. 4, 2025, 9 pages with translation.

Japanese Office Action from corresponding Application No. 2022-053983 mailed on Nov. 4, 2025, 8 pages with translation.

Japanese Decision to Grant from corresponding Application No. 2022-053982, mailed on Jan. 20, 2026, 3 pages with translation.

* cited by examiner

OPHTHALMOLOGIC APPARATUS

CROSS-REFERENCE TO RELATED APPLICATION

The present application is based on and claims priority to Japanese Patent Application No. 2022-053982 filed on Mar. 29, 2022, the disclosure of which is hereby incorporated by reference in its entirety.

FIELD OF THE INVENTION

The present disclosure relates to an ophthalmologic apparatus.

BACKGROUND

Conventionally known is an ophthalmologic apparatus that continuously measures spherical power of a subject eye while relaxing or relieving an accommodation of the subject eye by fogging the eye and presenting a fixation target at a predetermined presentation position, and determines whether or not the accommodation of the subject eye has been relaxed based on the measured spherical power (e.g., see JP11-346997).

In children and subjects or examinees who live with a high degree of near vision, crystalline lenses may be tense even in distance vision, and they may be in a state of so-called pseudomyopia. In the state of pseudomyopia, it is difficult to cancel or relax the accommodation of the subject eyes. Accordingly, when the fixation target is presented at a fixed presentation position, the accommodation of the subject eyes may have not been fully relaxed (pseudomyopia may have not been relieved) even though the change in the spherical power has converged. In short, there are differences among the examinees in the presentation position of the fixation target for the application of the fogging required to relax the accommodation of the subject eyes. Therefore, it is difficult to appropriately relax or relieve the accommodation of the subject eyes.

The present disclosure has been made by considering the above problem. An object of the present disclosure is to provide an ophthalmologic apparatus that can properly relax or relieve the accommodation of the subject eye.

SUMMARY

To achieve the object, an ophthalmologic apparatus includes an objective measurement optical system that is configured to objectively measure eye characteristics of a subject eye; an optotype projection system that is configured to present a fixation target to the subject eye at a predetermined presentation position and apply fog to the subject eye; and a controller that is configured to control the objective measurement optical system and optotype projection system. The controller is further configured to objectively measure the eye characteristics over time by changing a presentation position of the fixation target from the predetermined presentation position in a direction to increase an amount of fog and presenting the fixation target.

DETAILED DESCRIPTION

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

An ophthalmologic apparatus according to a first embodiment of the present disclosure will be described below with reference to the accompanying drawings.

The ophthalmologic apparatus 1 according to the first embodiment is a binocular open-field type ophthalmologic apparatus enabling simultaneous measurement of eye characteristics (ocular characteristics) of both eyes of an examinee or subject with the left and right eyes open. The ophthalmologic apparatus 1 of the first embodiment may measure the eye characteristics of each of the eyes by occluding the eye or turning off a fixation target.

Figure 1:
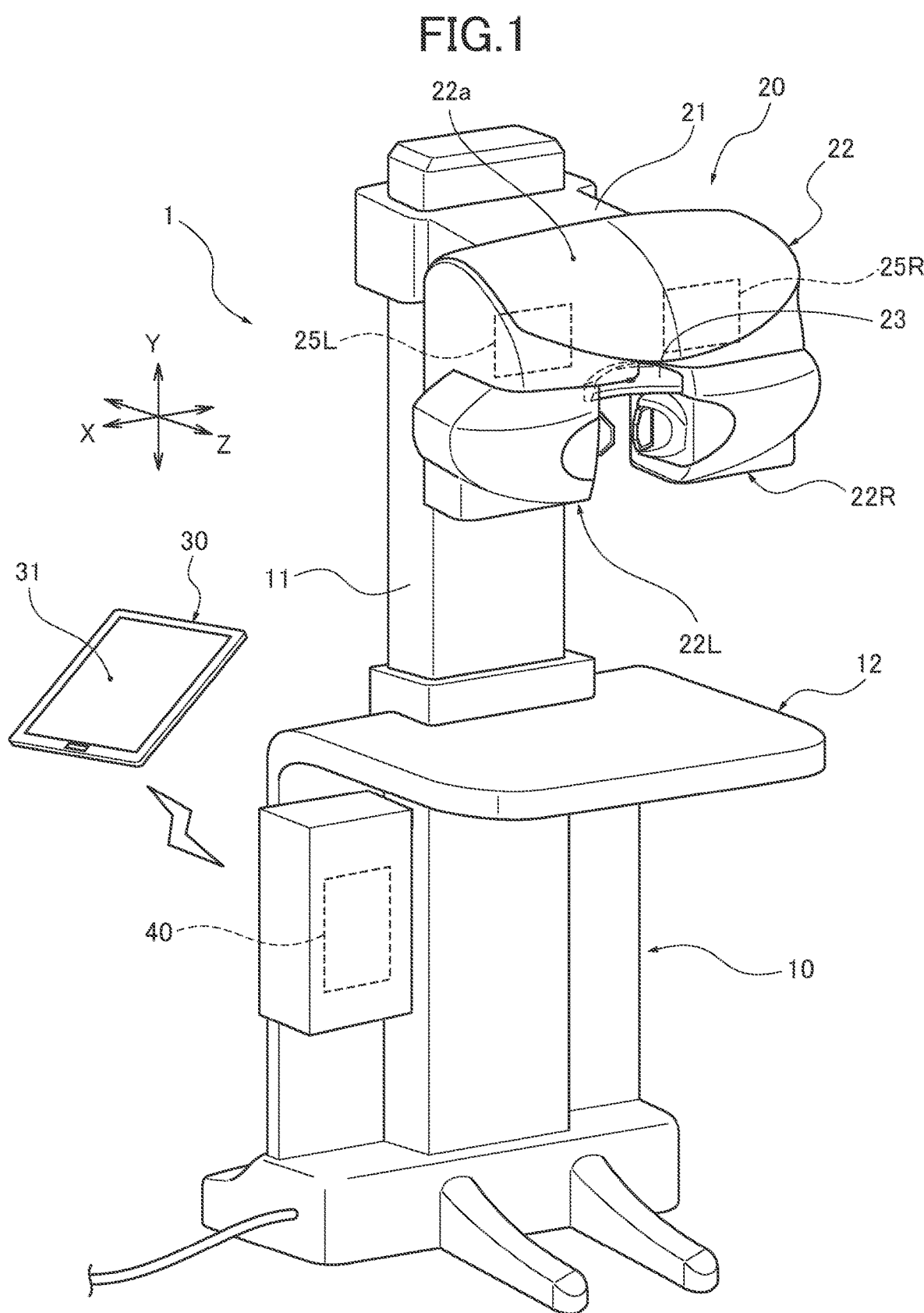
FIG. 1 is a perspective view of the entire configuration of an ophthalmologic apparatus according to a first embodiment.

As illustrated in FIG. 1, the ophthalmologic apparatus 1 of the first embodiment includes a support base 10, a measurement portion 20, a controller 40, and an examiner controller 30 (not illustrated). FIG. 1 shows X, Y, and Z directions. Hereinafter, a left-right direction is defined as the X direction, an up-down direction (vertical direction) is defined as the Y direction, and a direction (depth direction) orthogonal to the X and Y directions is defined as the Z direction. The directions are defined as seen from the examinee.

The measurement portion 20 includes a support base 10. The support base 10 includes a pillar 11 placed on the floor and an eye examination table 12 supported by the pillar 11. The eye examination table 12 is used to place devices such as the examiner controller 30 or tools used during the eye examination and support the posture of the examinee. The position in the Y direction (height) of the eye examination table 12 may be fixed or may be supported by the pillar 11 to be adjustable in the Y direction.

The measurement portion 20 includes an arm 21, a measurement head 22, and a forehead receiver 23. The arm 21 extends in the Z direction from the pillar 11 to a first side, which is an examinee side. The arm 21 has an end supported at the leading end of the pillar 11 and the other end to which the measurement head 22 is attached. Thus, the measurement head 22 is suspended from the pillar 11 via the arm 21 above the eye examination table 12. The arm 21 is movable in the Y direction with respect to the pillar 11. The arm 21 may be movable in the X direction and/or the Z direction with respect to the pillar 11.

The measurement head 22 is configured to measure the eye characteristics of subject eyes E. The measurement head 22 includes a driver 22a, a left measurement portion 22L, and a right measurement portion 22R. The left measurement portion 22L and the right measurement portion 22R are provided below the driver 22a and arranged in the X direction. The left measurement portion 22L and the right measurement portion 22R are paired to correspond to the left and right eyes of the examinee, respectively. The left measurement portion 22L includes a left measurement optical system 25L that is configured to measure the eye characteristics of the left eye of the examinee as the subject eye E (left subject eye). The right measurement portion 22R includes a right measurement optical system 25R that is configured to measure the eye characteristics of the right eye of the examinee as the subject eye E (right subject eye). A measurement result from the measurement head 22 is input to the controller 40.

The driver 22a is configured to individually drive the left measurement portion 22L and the right measurement portion 22R to move horizontally (in X direction), move vertically (in Y direction), rotate about the X-direction axis, and rotate about the Y-direction axis.

The ophthalmologic apparatus 1 of the first embodiment performs the objective and subjective measurements of the eye characteristics of the subject eye E. That is, the examiner can carry out the objective examination and the subjective examination with the ophthalmologic apparatus 1. In the objective examination, the subject eye E is irradiated with light and then information regarding the subject eye E (eye characteristics thereof) is measured based on the detection result of the reflected light. The objective examination includes the measurement for the acquisition of the eye characteristics of the subject eye E and photographing or capturing for the acquisition of an image of the subject eye E. For example, the objective examination includes objective refractive power measurement (refraction measurement), cornea shape measurement (kerato-measurement), eye pressure measurement, fundus photography or fundus shooting, photographing with optical coherence tomography (referred to as OCT hereinafter), measurement with OCT, and the like. In the subjective examination, the examinee is presented with the optotype, the eyechart, or the like, and then, the information regarding the subject eye E (eye characteristics) is measured based on the examinee's response to the presented optotype, the eyechart, or the like. For example, the subjective examination includes the subjective refraction measurements such as a far-point examination, a mid-point examination, a near-point examination, a contrast test, a glare test, a visual field test, and the like.

Figure 2:
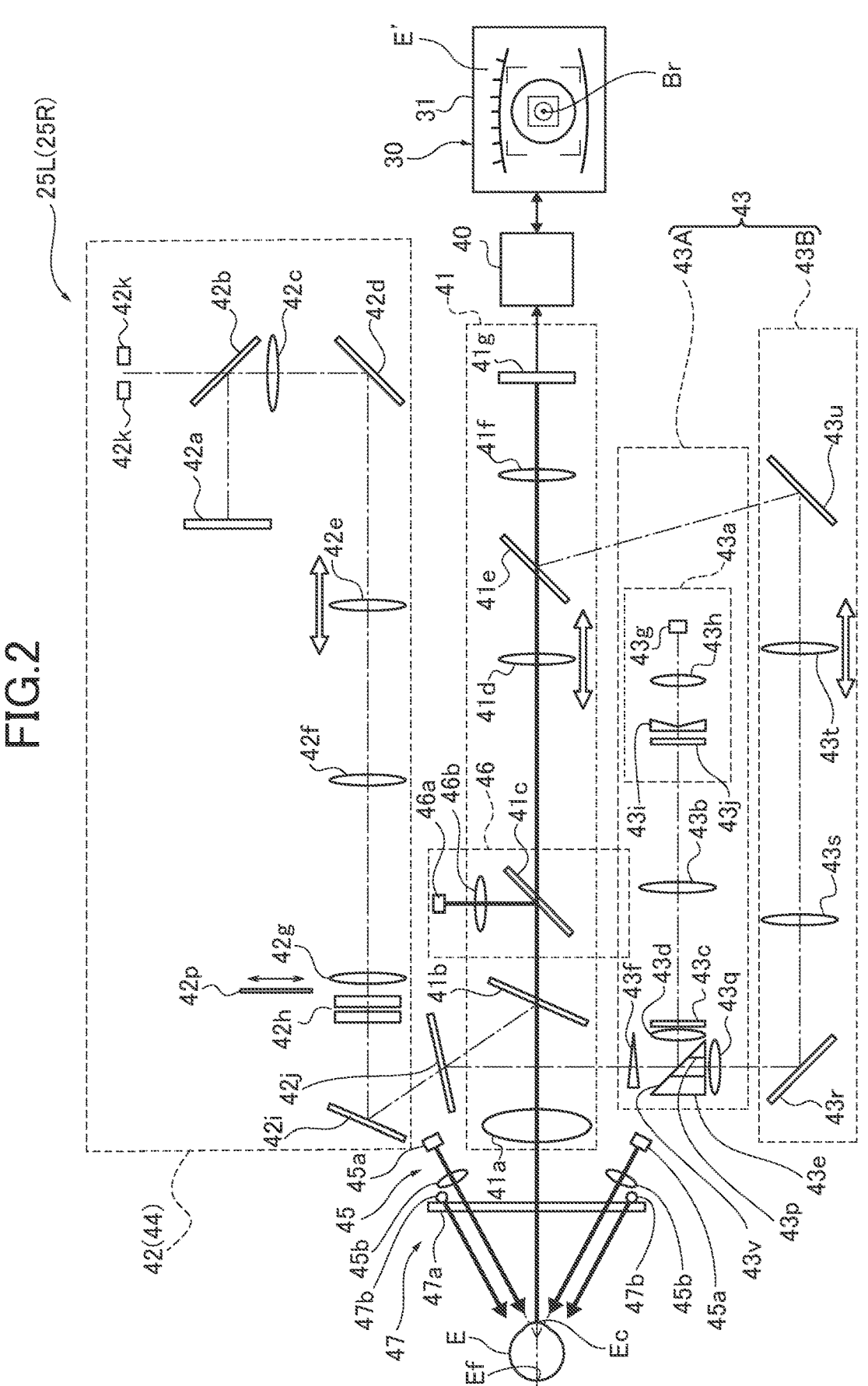
FIG. 2 illustrates a detailed configuration of a left measurement optical system of the ophthalmologic apparatus according to the first embodiment.

Therefore, as illustrated in FIG. 2, each of the left measurement optical system 25L and the right measurement optical system 25R in the measurement head 22 includes an observation system 41 that observes the anterior ocular segment of the subject eye E, an optotype projection system 42 that presents the optotype or the eye chart to the subject eye E, a refractive power measurement system 43 and a keratometry system 47 (left-eye objective measurement system or right-eye objective measurement system) that measures the eye characteristics of the subject eye E, and the like. Note that the keratometry system 47 is also referred to as the kerato-system 47 hereinafter. The detailed configurations of the left measurement optical system 25L and the right measurement optical system 25R will be described below.

The forehead receiver 23 is provided in the measurement portion 20 and is disposed between the left measurement portion 22L and the right measurement portion 22R. The forehead receiver 23 receives a part of the face (i.e., forehead) of the examinee to support his or her face in contact during the measurement of the eye characteristics. That is, the examinee in front of the eye examination table 12 places his or her forehead on the forehead receiver 23 and holds the face in a stable orientation or position. The position of the forehead receiver 23 is adjustable by moving the arm 21 in the Y direction with respect to the pillar 11.

The examiner controller 30 is an information processing device that is configured to receive an input operation from the examiner and output a control signal to the controller 40. The examiner controller 30 is, for example, a tablet terminal, a smartphone, or the like. The examiner controller 30 is removable from the measurement portion 20 to be carried by the examiner. The examiner controller 30 may be a laptop or desktop personal computer or may be a dedicated controller for the ophthalmologic apparatus 1. The examiner controller 30 exchanges information with the controller 40 via wireless communication or network communication.

The examiner controller 30 includes a display 31 as illustrated in FIG. 1, an operation-side control portion (not illustrated), and an input button (not illustrated). The display 31 is a touch panel display provided on the examiner controller 30, and the input button is provided. The operation-side control portion consists of a microcomputer in the examiner controller 30. The operation-side control portion is configured to control an image to be displayed on the display 31 based on the measurement result or detection result transmitted from the controller 40. The operation-side control portion outputs, to the controller 40, a control signal responsive to an operation to the input button.

The controller 40 is an information processing device provided below the eye examination table 12. Based on control signals transmitted from the examiner controller 30, the controller 40 controls, in a centralized manner, each part of the measurement portion 20 including the left measurement optical system 25L and the right measurement optical system 25R, each including the objective measurement optical system (refractive power measurement system 43 and kerato-system 47), the optotype projection system 42, and the like. The controller 40 transmits, to the examiner controller 30, the measurement results of the eye characteristics of the subject eye E measured by the measurement head 22.

Figure 3:
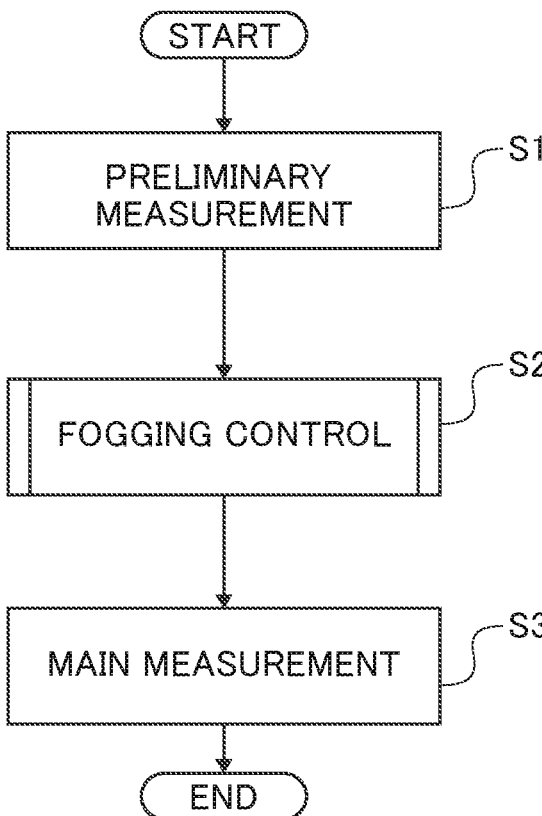
FIG. 3 is a flowchart showing a flow of a subjective examination and an objective examination performed by a controller according to the first embodiment.

As illustrated in FIG. 3, the controller 40 first performs the preliminary measurement (in Step S1) when measuring the eye characteristics by the objective examination and/or the subjective examination. Then, the controller 40 performs the fogging control (in Step S2) and then the main measurement (in Step S3) to measure the eye characteristics. The controller 40 of the first embodiment controls the measurement portion 20 during the fogging control to change or move the presentation position of the fixation target in the direction to increase the amount of fog (or degree of fogging) to present the fixation target to the subject eye E and objectively measure the eye characteristics of the subject eye E over time while applying the fog to the subject eye E. Note that the "amount of fog" is the amount or intensity of the fog applied to the subject eye E and is represented as a diopter conversion value that indicates the presentation position of the fixation target. The "amount of fog" is also referred to as the "degree of fogging" herein. The presentation position of the fixation target is in accordance with the amount of fog or the degree of fogging. The controller 40 moves or changes the presentation position of the fixation target in the direction of the far vision direction (to positive side) when increasing the amount of fog while the controller 40 moves or changes in the direction of the near vision (to negative side) when decreasing the amount of fog.

The controller 40 determines whether or not to continue changing the presentation position of the fixation target to the subject eye E based on the objective examination result of the eye characteristics measured over time at the time of the fogging control. In other words, the controller 40 determines whether or not to continue fogging by increasing the amount of fog based on the objective examination result of the eye characteristics measured over time at the time of the fogging control. Then, the controller 40 finishes changing the presentation position of the fixation target when the variation or fluctuation of the objective examination result has converged to a predetermined range set in advance. The controller 40 further changes the presentation position in the direction to increase the amount of fog and continuously applys the fog to the subject eye E with the increased amount of fog if the variation or fluctuation of the objective examination result does not converge to the predetermined range set in advance.

Figure 5:
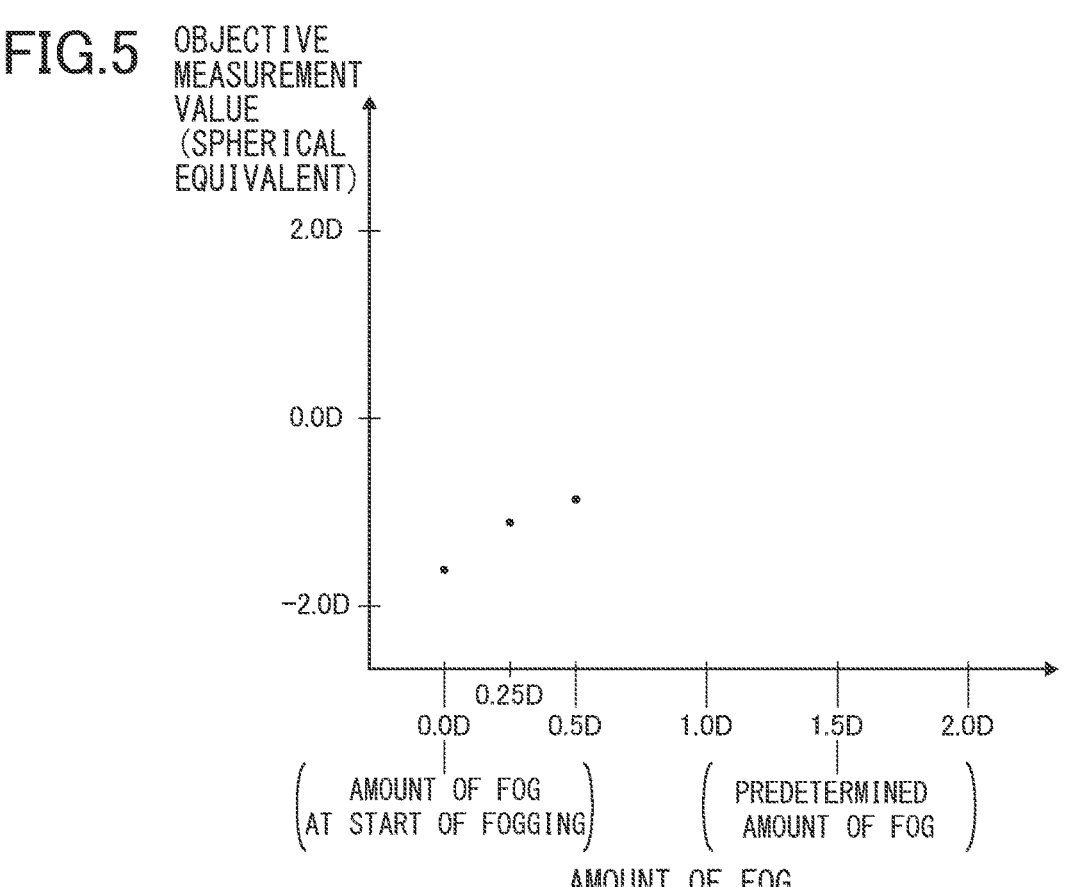
FIG. 5 is a first example of a graph showing a relationship between an amount of fog and objective measurement results of eye characteristics.
Figure 6:
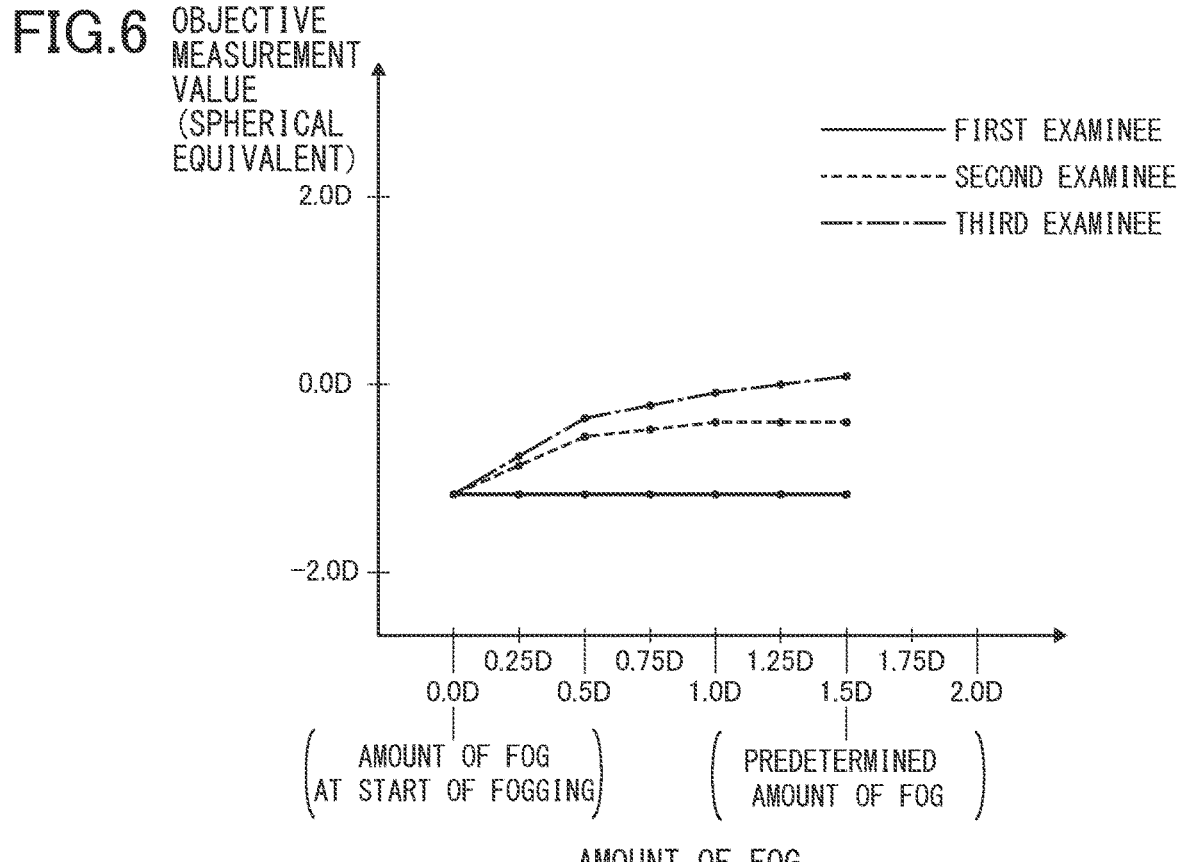
FIG. 6 is a second example of a graph showing a relationship between an amount of fog and objective measurement results of eye characteristics.
Figure 7:
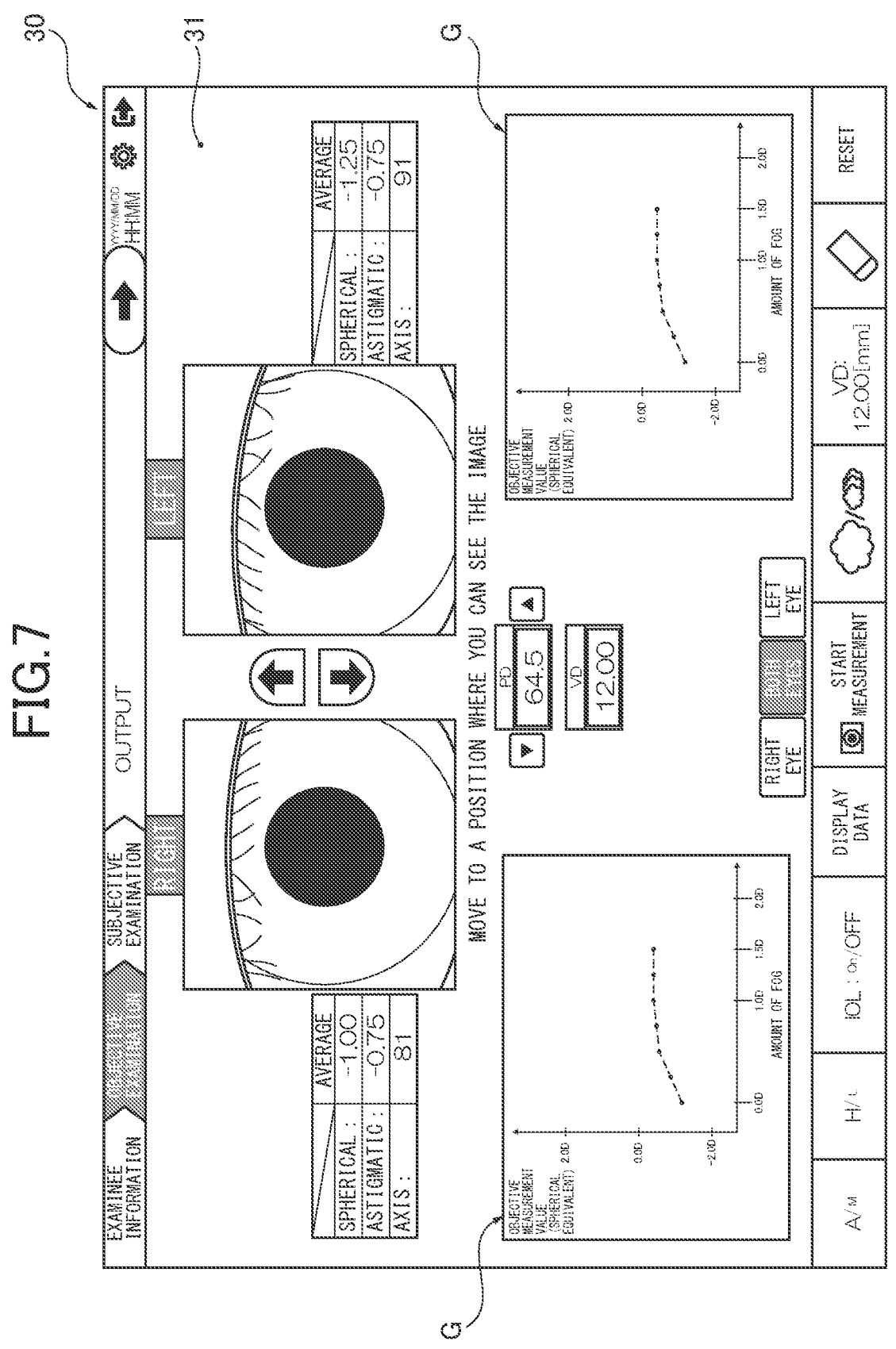
FIG. 7 illustrates a display of the ophthalmologic apparatus according to the first embodiment.

When performing the fogging control, the controller 40 shows, in a graph, the relationship between the amount of fog when the fixation target is presented and the objective examination results of the eye characteristics measured over time (see FIGS. 5 and 6). The graph G which shows the relationship between the amount of fog and the objective examination results is displayed on the display 31 of the examiner controller 30 as illustrated in FIG. 7.

Next, the detailed configurations of the left measurement optical system 25L and the right measurement optical system 25R will be described with reference to FIG. 2. The left measurement optical system 25L and the right measurement optical system 25R have the same configuration. Accordingly, only the left measurement optical system 25L will be described while the description of the right measurement optical system 25R is omitted.

As illustrated in FIG. 2, the left measurement optical system 25L includes the observation system 41, the optotype projection system 42, a subjective measurement optical system 44, a first alignment system 45, a second alignment system 46, and the refractive power measurement system 43 and the kerato-system 47 as the examples of the objective measurement optical system. Each of the subjective measurement optical system 44, the refractive power measurement system 43, and the kerato-system 47 is a measurement optical system that is configured to measure the eye characteristics of the subject eye E.

The observation system 41 includes an objective lens 41*a*, a first dichroic filter 41*b*, a first half mirror 41*c*, a first relay lens 41*d*, a second dichroic filter 41*e*, an image-forming lens 41*f*, and an imaging element (e.g., CCD) 41*g*.

The observation system 41 forms an image of a light flux reflected by the subject eye E (anterior ocular segment) on the imaging element 41*g* by the image-forming lens 41*f* via the objective lens 41*a*. As a result, on the imaging element 41*g*, a keratometry (kerato) ring light flux, a light flux of a first alignment light source 45*a*, and a light flux (bright spot image Br) of a second alignment light source 46*a*, which are described later, are projected to form an anterior-ocular-segment image E. The imaging element 41*g* captures the anterior-ocular-segment image E and acquires an image signal of the anterior-ocular-segment image E. The controller 40 displays, on the display 31 of the examiner controller 30, the anterior-ocular-segment image E or the like based on the image signal from the imaging element 41*g*.

The kerato-system 47 is provided ahead of the objective lens 41*a*. The kerato-system 47 is an example of the objective measurement optical system. The kerato-system 47 is configured to measure the cornea shape (radius of curvature) of the subject eye E. The kerato-system 47 includes a keratometry plate 47*a* and a keratometry ring light source 47*b*. Note that the keratometry plate 47*a* is also referred to as the kerato-plate 47*a* and the keratometry ring light source 47*b* is also referred to as the kerato-ring light source 47*b*. The kerato-plate 47*a* is a plate provided with a concentric slit about the optical axis of the observation system 41 and is provided near the objective lens 41*a*. The kerato-ring light source 47*b* is provided to correspond to the slit of the kerato-plate 47*a*.

In the kerato-system 47, the light flux from the kerato-ring light source 47*b* in lighting passes through the slit of the kerato-plate 47*a*, so that a kerato-ring light flux for measurement of the cornea shape (ring-shaped optotype for measurement of cornea curvature) is projected onto the subject eye E (cornea Ec). After reflected on the cornea Ec of the subject eye E, the kerato-ring light flux forms an image on the imaging element 41*g* by the observation system 41. Thus, the imaging element 41*g* receives and/or detects the ring-shaped image of the kerato-ring light flux. The controller 40 displays, on the display 31, the image of the kerato-ring light flux detected by the imaging element 41*g*. Furthermore, the controller 40 measures the cornea shape (radius of curvature) of the subject eye E based on an image signal detected by the imaging element 41*g*.

The first alignment system 45 is provided behind the kerato-system 47 (kerato-plate 47*a*). The first alignment system 45 is configured to position or align the optical system relative to the subject eye E in the direction along the optical axis of the observation system 41 (front-back direction or Z direction). The first alignment system 45 includes a pair of first alignment light sources 45*a* and a pair of first projection lenses 45*b*.

In the first alignment system 45, the light flux from each of the first alignment light sources 45*a* is made to the parallel light flux by the corresponding first projection lens 45*b*. Then, the parallel light flux is projected onto the cornea Ec of the subject eye E through an alignment hole provided at the kerato-plate 47*a*.

Based on the bright spot (bright-spot image Br) projected on the cornea Ec, the controller 40 or the examiner moves the left measurement portion 22L (or right measurement portion 22R) in the front-back direction to perform the alignment in the direction along the optical axis of the observation system 41 (front-back direction). During the alignment in the front-back direction, the controller 40 or the examiner adjusts the position of the left measurement portion 22L (or right measurement portion 22R) such that the ratio between the interval between two spot images by the first alignment light sources 45*a* and the diameter of the kerato-ring image on the imaging element 41*g* falls within a predetermined range.

The observation system 41 is provided with the second alignment system (parallel optical system) 46. The second alignment system 46 is configured to position or align the optical system relative to the subject eye E in the directions orthogonal to the optical axis of the observation system 41 (up-down and left-right directions, i.e., Y and X directions). The second alignment system 46 includes the second alignment light source 46*a* and a second projection lens 46*b*. The second alignment system 46 shares the first half mirror 41*c*, the first dichroic filter 41*b*, and the objective lens 41*a* with the observation system 41.

In the second alignment system 46, the light flux from the second alignment light source (point light source) 46*a* is made to the parallel light flux through the objective lens 41a. Then, the parallel light flux is projected onto the cornea Ec of the subject eye E. The parallel light flux projected from the second alignment system 46 onto the cornea Ec of the subject eye E forms a bright spot of the alignment light at a substantially middle position between the cornea apex and the center of curvature of the cornea Ec.

Based on the bright spot (bright-spot image Br) projected on the cornea Ec, the controller 40 or the examiner moves the left measurement portion 22L (or right measurement portion 22R) in the up-down direction or the left-right direction to perform the alignment in the directions (up-down and left-right directions) orthogonal to the optical axis of the observation system 41.

The optotype projection system 42 projects an optotype (fixation target), leading to presentation to the fundus Ef of the subject eye E to bring the subject eye E into fixation or fog. The subjective measurement optical system 44 projects the optotype onto the subject eye E during the subjective examination. In the ophthalmologic apparatus 1 of the first embodiment the optotype projection system 42 and the subjective measurement optical system 44 share the optical elements in the optical system.

The optotype projection system 42 (subjective measurement optical system 44) includes a display 42a, a second half mirror 42b, a second relay lens 42c, a first reflective mirror 42d, a first focusing lens 42e, a third relay lens 42f, a first field lens 42g, a variable cross-cylinder lens (also referred to as VCC hereinafter) 42h, a second reflective mirror 42i, and a third dichroic filter 42j. The optotype projection system 42 (subjective measurement optical system 44) shares the first dichroic filter 41b and the objective lens 41a with the observation system 41. Furthermore, the optotype projection system 42 (subjective measurement optical system 44) includes at least two glare light sources 42k that irradiate the subject eye E with glare light, around the optical axis and on an optical path different from the optical path to the display 42a for the subjective examination.

The display 42a displays the fixation target or the point-like optotype as the optotype for fixing a line of sight for the objective examination and for the fogging to the subject eye E and displays the subjective-examination optotype for the subjective examination of the eye characteristics of the subject eye E (e.g., visual acuity value, correction power, far-point power, and near-point power). The display 42a may be an organic electroluminescence (EL) display or a liquid crystal display (LCD). The display 42a displays any image in response to the control of the controller 40. The display 42a is provided at a position conjugate with the fundus Ef of the subject eye E on the optical path of the optotype projection system 42 (subjective measurement optical system 44).

The first focusing lens 42e moves forward or backward along the optical axis by a drive motor (not illustrated) controlled by the controller 40. The controller 40 moves the first focusing lens 42e toward the subject eye E, so that the refractive index can be displaced to the negative side. The controller 40 moves the first focusing lens 42e in the direction away from the subject eye E, so that the refractive index can be displaced to the positive side (in far view direction). Therefore, the controller 40 changes the presentation position of the optotype displayed on the display 42a by the forward or backward movement of the first focusing lens 42e, so that the examination distance is changed from the presentation position of the optotype to the subject eye E.

The optotype projection system 42 (subjective measurement optical system 44) includes a pinhole plate 42p at a position substantially conjugate with the pupil of the subject eye E on the optical path (between first field lens 42g and VCC 42h in example of FIG. 2). The pinhole plate 42p is formed of a plate member provided with a through-hole. The pinhole plate 42p is controlled by the controller 40 to be inserted into or removed from the optical path of the optotype projection system 42 (subjective measurement optical system 44). The through-hole is located on the optical axis when the pinhole plate 42p is inserted in the optical path. Insertion of the pinhole plate 42p into the optical path during the subjective examination enables a pinhole test to determine whether or not the subject eye E can be corrected with glasses. Note that the pinhole plate 42p is not limited to the configuration illustrated in FIG. 2 as long as it is provided at a position substantially conjugate with the pupil of the subject eye E on the optical path.

The optotype to be displayed on the display 42a for the subjective examination is not particularly limited, provided that the optotype can be used in the eye examination. For example, the optotype includes a Landolt ring, a Snellen chart, an E chart, and the like. The optotype may be a still image or a moving image. The ophthalmologic apparatus 1 of the first embodiment including the display 42a, such as an LCD, enables the display of the desired optotype in shape, mode, and contrast at a predetermined examination distance and various types of detailed eye examinations. The ophthalmologic apparatus 1 of the first embodiment includes two displays 42a corresponding to the left and right subject eyes E, respectively. Thus, the ophthalmologic apparatus 1 enables the display of the optotype for parallax corresponding to a predetermined examination distance (presentation position) and the simple and precise stereoscopic vision examination with the natural orientation of the visual axis.

Furthermore, the optotype projection system 42 presents the fixation target (optotype) to the subject eye E at a predetermined presentation position when fogging the subject eye E. The presentation position of the fixation target (optotype) is set in accordance with the amount of fog or the degree of fogging to the subject eye E.

The refractive power measurement system 43 is an example of the objective measurement optical system and measures the refractive power of the subject eye E. In the first embodiment, the refractive power measurement system 43 has a function to project a predetermined measurement pattern onto the fundus Ef of the subject eye E and a function to detect an image of the measurement pattern projected on the fundus Ef. That is, the refractive power measurement system 43 includes a ring-shaped light flux projection system 43A that projects a ring-shaped measurement pattern onto the fundus Ef of the subject eye E and a ring-shaped light flux reception system 43B that receives and/or detects the reflected light of the ring-shaped measurement pattern from the fundus Ef.

The ring-shaped light flux projection system 43A includes a refraction light-source unit 43a, a fourth relay lens 43b, an eye-ring diaphragm 43c, a second field lens 43d, a holed prism 43e, and a rotary prism 43f. The ring-shaped light flux projection system 43A shares the third dichroic filter 42j with the optotype projection system 42 (subjective measurement optical system 44) and shares the first dichroic filter 41b and the objective lens 41a with the observation system 41. The refraction light-source unit 43a includes a refraction-measurement light source 43g for the refraction measurement including, for example, an LED, a collimator lens 43h, a conical prism 43i, and a ring-pattern formation plate 43*j*. The refraction light-source unit 43*a* is controlled by the controller 40 to move integrally on the optical axis of the refractive power measurement system 43.

The ring-shaped light flux reception system 43B includes a hole 43*p* of the holed prism 43*e*, a third field lens 43*q*, a third reflective mirror 43*r*, a fifth relay lens 43*s*, a second focusing lens 43*t*, and a fourth reflective mirror 43*u*. The ring-shaped light flux reception system 43B shares the objective lens 41*a*, the first dichroic filter 41*b*, the second dichroic filter 41*e*, the image-forming lens 41*f*, and the imaging element 41*g* with the observation system 41. Furthermore, the ring-shaped light flux reception system 43B shares the third dichroic filter 42*j* with the optotype projection system 42 (subjective measurement optical system 44) and shares the rotary prism 43*f* and the holed prism 43*e* with the ring-shaped light flux projection system 43A.

When the refractive power measurement system 43 measures the refractive power of the subject eye E, the controller 40 first turns on the refraction-measurement light source 43*g*. Then, the controller 40 moves the refraction light-source unit 43*a* of the ring-shaped light flux projection system 43A and the second focusing lens 43*t* of the ring-shaped light flux reception system 43B in the optical axis direction. Next, in the ring-shaped light flux projection system 43A, the refraction light-source unit 43*a* emits a ring-shaped measurement pattern. The measurement pattern travels through the fourth relay lens 43*b*, the eye-ring diaphragm 43*c*, and the second field lens 43*d* to the holed prism 43*e*. Then, the measurement pattern is reflected by a reflective face 43*v* of the holed prism 43*e* and guided to the third dichroic filter 42*j* through the rotary prism 43*f*. The ring-shaped light flux projection system 43A guides the measurement pattern to the objective lens 41*a* through the third dichroic filter 42*j* and the first dichroic filter 41*b*, so that the ring-shaped measurement pattern is projected on the fundus Ef of the subject eye E.

The ring-shaped light flux reception system 43B condenses the ring-shaped measurement pattern formed on the fundus Ef with the objective lens 41*a* and then guides the ring-shaped measurement pattern to the hole 43*p* of the holed prism 43*e* through the first dichroic filter 41*b*, the third dichroic filter 42*j*, and the rotary prism 43*f*. Next, the ring-shaped light flux reception system 43B guides the measurement pattern through the third field lens 43*q*, the third reflective mirror 43*r*, the fifth relay lens 43*s*, the second focusing lens 43*t*, the fourth reflective mirror 43*u*, the second dichroic filter 41*e*, and the image-forming lens 41*f* to form the image on the imaging element 41*g*. Thus, the imaging element 41*g* detects the image of the ring-shaped measurement pattern, and the controller 40 displays, on the display 31, the image of the measurement pattern detected by the imaging element 41*g*. Then, the controller 40 measures the spherical power, the cylindrical power, and the axial angle as refractive power based on an image signal from the imaging element 41*g*.

Note that the configurations of the refractive power measurement system 43, the first alignment system 45, the second alignment system 46, the kerato-system 47, and the like, as well as the principle of measurement of the subjective examination and the cornea shape (kerato) are known, and thus the detailed descriptions thereof are omitted.

Figure 4:
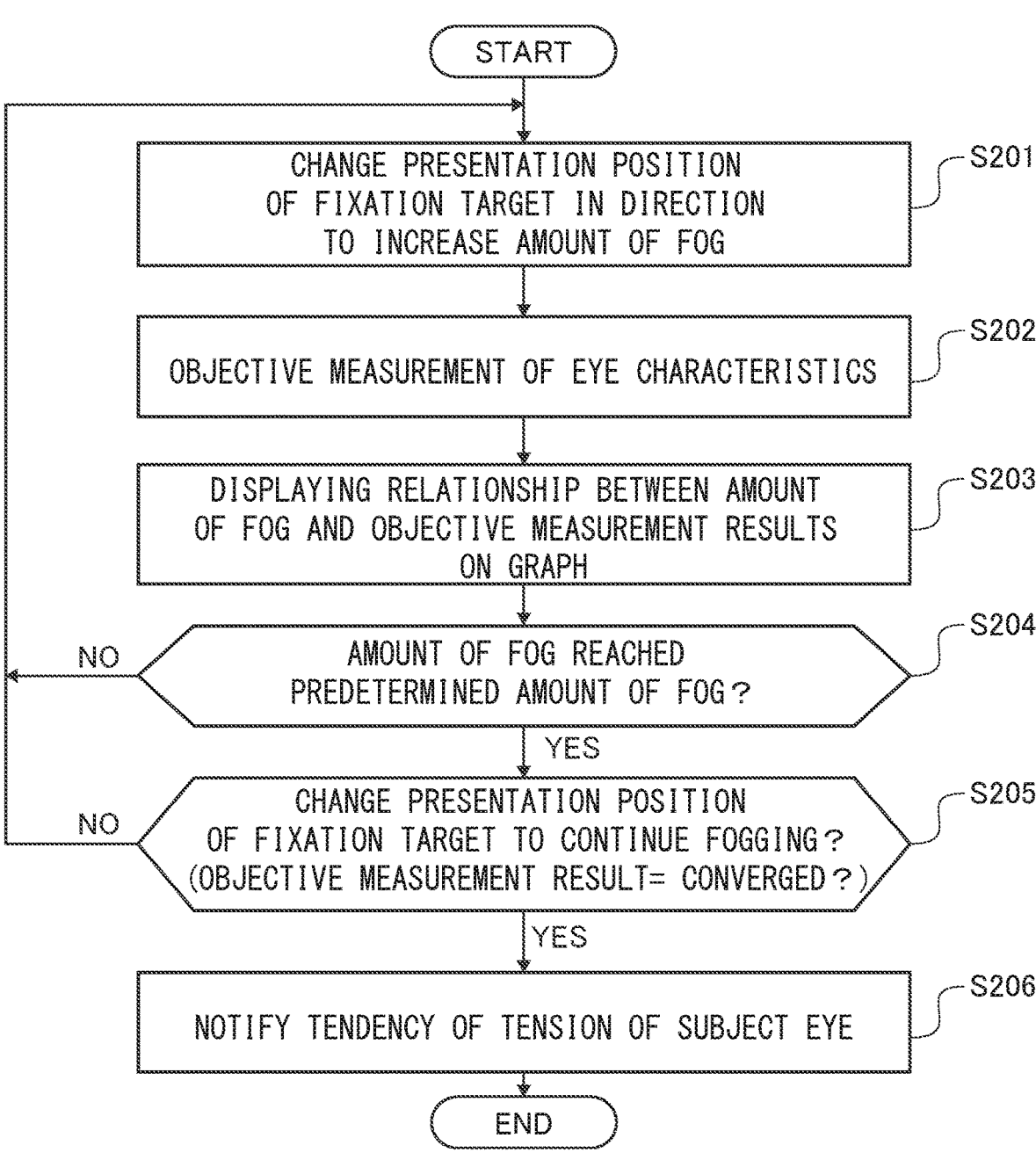
FIG. 4 is a flowchart showing a flow of a fogging control by the controller according to the first embodiment.

Next, the procedure of the fogging control by the controller 40 of the first embodiment will be described with reference to the flowchart illustrated in FIG. 4.

As illustrated in FIG. 3, the fogging control (Step S2) is performed between the preliminary measurement (Step S1)

and the main measurement (Step S3) when the objective examination and/or the subjective examination are carried out.

The "preliminary measurement" corresponds to a step of focusing the subject eye E on a fogging start position. For example, the "preliminary measurement" is performed in accordance with the following procedure. That is, the controller 40 computes the tentative spherical power S and astigmatic power C for the subject eye E based on the captured image of the ring image obtained with the refractive power measurement system 43. Then, the controller 40 controls the second focusing lens 43*t* based on the computation result of the tentative spherical power S and astigmatic power C and moves the focal position of pattern light to the position corresponding to the spherical equivalent (S+C/2) (position corresponding to tentative far point, namely, fogging start position).

The "main measurement" is a step of measuring predetermined eye characteristics. For example, for the objective refraction measurement (refraction measurement), the "main measurement" is performed as follows. That is, the controller 40 controls the ring-shaped light flux projection system 43A to project the ring-shaped measurement pattern onto the fundus Ef of the subject eye E to which the fog has been applied. Then, the controller 40 controls the ring-shaped light flux reception system 43B to receive and/or detect the reflected light of the ring-shaped measurement pattern from the fundus Ef and measures the spherical power, the cylindrical power, and the axis angle as the refractive power based on the image signal from the imaging element 41*g*.

The ophthalmologic apparatus 1 of the first embodiment is the binocular open-type ophthalmologic apparatus that can simultaneously measure the eye characteristics of both eyes. Therefore, each step of the preliminary measurement, the fogging control, and the main measurement can be performed on the left and right subject eyes E at the same time.

Also, the ophthalmologic apparatus 1 of the first embodiment decides an "increase amount of fog", a "prescribed amount of fog", and a "threshold for determining fluctuation of the objective examination result" in advance at the time of the fogging control. The "increase amount of fog" is the amount of fog to be increased when the presentation position of the fixation target is changed. For example, the amount of fog is increased, for example, by 0.25D (diopter) to the positive side (far view direction). The "prescribed amount of fog" is the amount of fog that is a trigger for determining whether the objective examination result measured during the fogging control has converged or not. The "prescribed amount of fog" may be set as desired. The "prescribed amount of fog" is set, for example, by 1.5D (diopter) to the positive side (far view direction) when the amount of fog at the beginning of the fogging is set to 0.0D (diopter). The "threshold for determining the fluctuation of the objective examination result" is a predetermined range for determining whether or not the objective examination result measured during the fogging control has converged. For example, the "threshold for determining the fluctuation of the objective examination result" is set to ±0.1D (diopter).

In Step S201 for the fogging control, the controller 40 changes or moves the presentation position of the fixation target in the direction to increase the amount of fog. Then, the process proceeds to Step S202. An amount of change in the presentation position of the fixation target is decided in advance in accordance with the "increase amount of fog". Specifically, the controller 40 changes or moves the presentation position of the fixation target from the currently set position to a position to increase the amount of fog by a predetermined amount (e.g., 0.25D to positive side). As a result, the fixation target is moved to the position that increases the amount of fog (position shifted by 0.25D to positive side). Note that the "increase amount of fog" (amount of change in presentation position of fixation target) may be decided at the time of each change in accordance with the objective examination result of the eye characteristics measured in Step S202. Since the presentation position of the fixation target has been changed, the fog is applied to the subject eye E at the changed fixation target position where the amount of fog increases.

After fogging by changing the presentation position of the fixation target to increase the amount of fog in Step S201, the controller 40 objectively measures the eye characteristics of the subject eye E. In other words, the controller 40 performs the objective examination in Step S202. Then, the process proceeds to Step S203. The objective examination of the subject eye E is the objective refraction measurement (ref measurement) using the refractive power measurement system 43, for example. Thereby, the controller 40 objectively measures the eye characteristics by changing the presentation position of the fixation target in the direction to increase the amount of fog and presenting the fixation target at the changed presentation position.

After the objective examination in Step S202, in Step S203, the controller 40 shows, in the graph G, the relationship between the current amount of fog increased in Step S201 and the objective examination results of the eye characteristics measured in Step S202. Then, the process proceeds to Step S204. The graph G which shows the relationship between the amount of fog and the objective examination results may be shown by plotting the values as illustrated in FIG. 5. Alternatively, the graph G may be shown by connecting the plotted values with polygonal lines as illustrated in FIG. 6. Note that in FIG. 6, the results for the examinees are shown together on the graph G since the objective examination results differ from each other for each of the examinees. The graph G may be generated for each of the examinees. The graph G is displayed on the display 31 as illustrated in FIG. 7. Also, a range of astigmatism may be shown on the graph G in the case where the objective examination results are indicated, for example, by the spherical equivalent.

After showing the graph in Step S203, the controller 40 determines in Step S204 whether or not the amount of fog at the time of the objective examination in Step S202 has reached "the prescribed amount of fog" set in advance. In other words, in Step S204, the controller 40 determines whether or not the current amount of fog increased in Step S201 has reached "the prescribed amount of fog". In the case of YES (i.e., current amount of fog has reached prescribed amount of fog), the process proceeds to Step S205. In the case of NO (i.e., current amount of fog has not reached prescribed amount of fog), the process returns to Step S201.

In the case where the process returns to Step S201 from Step S204, the controller 40 again changes the presentation position of the fixation target in the direction to increase the amount of fog. Thereby, the fog is applied (fogging is performed) to the subject eye E again at the fixation target position where the amount of fog is further increased. Then, the process proceeds to Step S202, and the controller 40 objectively measures the eye characteristics of the subject eye E. Specifically, the change in the presentation position of the fixation target and the objective examination associated with the change are repeated until the amount of fog reaches "the prescribed amount of fog" set in advance. As a result, the controller 40 objectively measures the eye characteristics over time by changing the presentation position of the fixation target in the direction to increase the amount of fog and presenting the fixation target at the changed presentation position.

After the determination that the amount of fog has reached "the prescribed amount of fog" set in advance in Step S204, the controller 40 determines in Step S205 whether or not to change the presentation position of the fixation target and continue fogging in accordance with the objective examination result measured in Step S202. In other words, in Step S205, the controller 40 measures whether or not the objective examination result of the eye characteristics measured in Step S202 has converged.

In the case where the amount of fluctuation in the objective examination results is greater than a predetermined range (e.g., ±0.1D) between the last measurement and the previous measurement (e.g. in case of third examinee illustrated in FIG. 6), the controller 40 determines that the crystalline lens is in a state of tension and the fogging is insufficient. In this case, the controller 40 determines that "the objective examination result has not converged (continuation of fogging)". That is, the controller 40 determines NO in Step S205 and then, the process returns to Step S201. On the other hand, in the case where the amount of fluctuation in the objective examination results between the last measurement and the previous measurement is relatively small (e.g., when the amount of fluctuation falls within above predetermined range, in case of first and second examinees illustrated in FIG. 6), the controller 40 determines that the tension of the crystalline lens has been relieved and the fogging is sufficient. In this case, the controller 40 determines that "the objective examination result has been converged (end of fogging)". That is, the controller 40 determines YES in Step S205 and then, the process proceeds to Step S206. Note that the controller 40 may analyze the fluctuation in the amount of fog from the fogging start position and determine that "the objective examination result has been converged" when the fluctuation in the amount of fog is presumed to have decreased.

Also in the case where the process returns to Step S201 from Step S205, the controller 40 again changes the presentation position of the fixation target in the direction to increase the amount of fog. Then, the fog is again applied to the subject eye E at the fixation target position where the amount of fog is further increased. The process proceeds to Step S202, and the controller 40 objectively measures the eye characteristics of the subject eye E. Specifically, the change in the presentation position of the fixation target and the objective examination associated with the change are repeated until it is determined that the objective examination result has converged. As a result, the controller 40 objectively measures the eye characteristics over time by changing the presentation position of the fixation target in the direction to increase the amount of fog and presenting the fixation target at the changed presentation position.

After the determination that the objective examination result has converged in Step S205, the controller 40 presumes a tendency of tension (also referred to as tension tendency hereinafter) of the subject eye E in accordance with the objective examination result of the eye characteristics measured in Step S202 and notifies the tension tendency to the examiner and/or the examinee in Step S206. Then, the process proceeds to END. Here, the "tension tendency of the subject eye E" is information that indicates the tendency of the subject eye E to reaccommodate (i.e., ease of reaccommodation or the degree of tension relief of the subject eye E). The "tension tendency of the subject eye E" is obtained from the amount of fluctuation (amount of variation) of the objective examination result from the beginning of the fogging. The controller 40 may presume that the tension tendency of the subject eye E is "prone to be tension (fogging is insufficient and the degree of relief is relatively low, so reaccommodation is likely to occur)" when the amount of fluctuation of the objective examination result from the beginning of the fogging is equal to or greater than a predetermined amount (e.g., +0.5D) or the controller 40 may presume that the tension tendency of the subject eye E is "prone to be tension (fogging is insufficient and the degree of relief is relatively low, so reaccommodation is likely to occur)" when the sum of the amount of fluctuation in the objective measurement results each time the fixation target position is changed is equal to or greater than a predetermined amount (e.g., +1.0D). In contrast, the controller 40 may presume that the tension tendency of the subject eye E is "not prone to be tension (tension is sufficiently relieved and reaccommodation is not likely to occur)" when the amount of fluctuation of the objective examination result from the beginning of the fogging is equal to or less than the predetermined amount (e.g., +0.5D) or the controller 40 may presume that the tension tendency of the subject eye E is "not prone to be tension (tension is sufficiently relieved and reaccommodation is not likely to occur)" when the sum of the amount of fluctuation in the objective measurement results each time the fixation target position is changed is equal to or less than a predetermined amount (e.g., +1.0D).

The notification of "the tension tendency of the subject eye E" may be made by display on the display 31, by voice, or the like. If the degree of astigmatism of the subject eye E is relatively large, the depth of focus increases, which may affect the amount of fluctuation of the objective examination result. Therefore, the degree of astigmatism may be noticed if the degree of astigmatism is relatively large (e.g., 1.0D or more).

Hereinafter, the operations, and effects of the ophthalmologic apparatus 1 of the first embodiment will be described.

The ophthalmologic apparatus 1 of the first embodiment performs the fogging control (in Step S2) between the preliminary measurement (Step S1) and the main measurement (in Step S3) when measuring the eye characteristics of the subject eye E. That is, the controller 40 changes or moves the presentation position of the fixation target in the direction to increase the amount of fog in accordance with the predetermined "increased amount of fog" (Step S201) after the preliminary measurement (Step S1). Accordingly, the fog is applied to the subject eye E with the increased amount of fog and the controller 40 objectively measures the eye characteristics of the fogged subject eye E (Step S202).

Next, the controller 40 shows the relationship between the amount of fog and the objective examination result in the graph (Step S203). Then, the controller 40 determines whether or not the amount of fog has reached "the prescribed amount of fog" (Step S204). Further, in the case where the amount of fog has reached "the prescribed amount of fog", the controller 40 determines whether or not to continue fogging after changing the presentation position of the fixation target based on whether or not the objective examination result has converged (Step S205).

In the case where the objective examination result has converged (i.e., determination is made not to continue fogging after changing presentation position of fixation target), the controller 40 presumes the tension tendency of the subject eye E based on the objective examination result and notifies it to the examiner and/or the examinee (Step S206). Subsequently, the controller 40 performs the main measurement (Step S3).

The controller 40 repeats changing the presentation position of the fixation target in the direction to increase the amount of fog and the objective examination until it is determined not to continue changing the presentation position of the fixation target after the amount of fog has reached "the prescribed amount of fog" and the objective examination result has converged.

In the fogging control (Step S2), the ophthalmologic apparatus 1 of the first embodiment changes or moves the presentation position of the fixation target in the direction to increase the amount of fog and presents the fixation target to the subject eye E. Then, the ophthalmologic apparatus 1 objectively measures the eye characteristics over time while fogging the subject eye E. Specifically, the fog is applied to the subject eye E while changing the fixation target position in the direction to increase the amount of fog, and the eye characteristics of the subject eye Eat that time are objectively measured over time. Therefore, the controller 40 can perform additional fogging, if necessary, while presuming the tension state of the subject eye E based on the objective examination result.

In the example illustrated in FIG. 6, for example, in the case of the first examinee shown with a solid line, there is no difference between the objective measurement value (spherical equivalent) with the predetermined amount of fog at the beginning of the fogging and the objective measurement value (spherical equivalent) after increasing the amount of fog to the positive side by 0.25D (diopter) from the amount of fog at the beginning of the fogging. In other words, in the case of the first examinee, the fluctuation of the objective examination result has already fallen within a predetermined range when the fixation target is presented at the position where the amount of fog becomes a predetermined amount of fog at the beginning and the fog is applied to the subject eye E. Therefore, it is possible for the controller 40 to determine that "the objective examination result" has converged with the fixation target presented at the fogging start position and the tension of the subject eye E of the first examinee is relaxed when the fixation target is presented at the fogging start position and the fog is applied to the subject eye E. Therefore, in the case of the first examinee, the tension of the subject eye E has been relaxed when the amount of fog has reached "the prescribed amount of fog", so that the controller 40 can determine that the additional fogging with the increase in the amount of fog is unnecessary.

In the case of the second examinee shown with a dotted line in FIG. 6, there is no difference between the objective measurement value (spherical equivalent) after increasing the amount of fog to the positive side by 1.0D (diopter) from the amount of fog at the beginning of the fogging and the objective measurement value (spherical equivalent) after increasing the amount of fog to the positive side by 1.25D (diopter) from the amount of fog at the beginning of the fogging. In other words, in the case of the second examinee, the fluctuation of the objective examination result falls within the predetermined range when the fixation target is presented at the position where the amount of fog is increased by 1.0D (diopter) from the amount of fog at the beginning of the fogging and the fog is applied to the subject eye E. Therefore, the tension of the subject eye E of the second examinee is relaxed when the fixation target is presented at the position where the amount of fog is increased by 1.0D (diopter) from the amount of fog at the beginning of the fogging and the fog is applied to the subject eye E. Therefore, in the case of the second examinee, the tension of the subject eye E has been relaxed when the amount of fog has reached the "the prescribed amount of fog", so that it is possible for the controller 40 to determine that the additional fogging with the increase in the amount of fog is unnecessary.

On the other hand, in the case of the third examinee shown with a dashed line in FIG. 6, the objective measurement value (spherical equivalent) continues to vary or fluctuate even when the presentation position of the fixation target is gradually changed or moved in the direction to increase the amount of fog to the positive side (far view direction). Therefore, in the case of the third examinee, it is not determined that "the objective examination result has converged" since the fluctuation of the objective examination result does not fall within the predetermined range even when the fixation target is presented at the position where the amount of fog is increased by +1.5D (diopter) from the amount of fog at the beginning of the fogging and the fog is applied to the subject eye E. Therefore, in the case of the third examinee, the tension of the subject eye E is not relaxed even if the amount of fog has reached "the prescribed amount of fog", so that it is possible for the controller 40 to determine that the additional fogging with the increase in the amount of fog is necessary.

Thereby, the ophthalmologic apparatus 1 can properly relieve or relax the accommodation of the subject eye E even with the state of pseudomyopia, for example. Also, the controller 40 or the examiner can understand the relationship between the presentation position of the fixation target and the objective examination result over time. Therefore, the controller 40 or the examiner can determine how much of the amount of fog (fixation target position) relieves the crystalline lens of the subject eye E based on the presentation position of the fixation target at the timing, for example, when the objective examination result has converged. Also, the controller 40 or the examiner can determine whether or not the examinee has pseudomyopia depending on whether or not the objective examination results fluctuate with the changes in the presentation position of the fixation target. In addition, the ophthalmologic apparatus 1 can inform whether there is a possibility of insufficient fogging and the like in accordance with the fluctuation of the objective examination result.

Also, in the ophthalmologic apparatus 1 of the first embodiment, the controller 40 determines whether or not to change the presentation position of the fixation target and continue fogging based on the objective examination result of the eye characteristics measured over time (Step S205). That is, the ophthalmologic apparatus 1 determines whether to start the main measurement or not based on the objective examination result of the eye characteristics measured over time during the fogging control. This allows the next step (i.e., main measurement) to start immediately when the fog is properly applied to the subject eye E and prevents the unnecessary prolongation of the examination time and the unnecessary increase in the stress on the examinee.

Also, in the ophthalmologic apparatus 1 of the first embodiment, the controller 40 presumes the tension tendency of the subject eye E and notifies it based on the objective examination result of the eye characteristics measured over time (Step S206). Thereby, the examiner and/or the examinee can easily understand the tension tendency of the subject eye E. Then, the examiner or the like can perform the main measurement and apply the fog again with the understanding of the tension tendency of the subject eye E.

That is, in the case where the amount of fluctuation in the objective examination result from the beginning of the fogging is relatively large (in case where tension tendency of subject eye E is presumed to be "prone to be tension"), the accommodation is likely to fluctuate during the main measurement such as the subjective measurement even if the tension is relaxed at the end of the fogging control. Accordingly, it is necessary to pay attention to the tension of the subject eye E during the main measurement. In the ophthalmologic apparatus 1 of the first embodiment, the examiner or the like can understand the tension tendency of the subject eye E before the main measurement. Accordingly, the examiner or the like can perform the main measurement while monitoring the tension of the subject eye E.

Also, in the ophthalmologic apparatus 1 of the first embodiment, the controller 40 shows, in the graph, the relationship between the amount of fog when presenting the fixation target and the objective examination result of the eye characteristics measured over time (Step S203). Thereby, the examiner and/or the examinee can easily understand the relationship between the amount of fog and the objective examination result of the subject eye E and more properly understand the tension of the subject eye E.

Also, the ophthalmologic apparatus 1 of the first embodiment includes the keratometry system (kerato-system) 47 and the refractive power measurement system 43 of the left measurement optical system 25L that objectively measures the eye characteristics of the left subject eye E, and the kerato-system 47 and the refractive power measurement system 43 of the right measurement optical system 25R that objectively measures the eye characteristics of the right subject eye E. That is, the ophthalmologic apparatus 1 of the first embodiment is the binocular open-field type ophthalmologic apparatus that measures each of the left and right subject eyes E of the examinee. Thereby, the ophthalmologic apparatus 1 can simultaneously measure the eye characteristics of both eyes, simultaneously apply the fog to both eyes, and set the presentation positions of the fixation targets differently for the left and right eyes. Therefore, the accommodation for each of the left and right subject eyes E can be properly relaxed or relieved.

The ophthalmologic apparatus 1 of the first embodiment is the binocular open-field type ophthalmologic apparatus. Accordingly, the ophthalmologic apparatus 1 can simultaneously show the graphs G for both eyes at the same time as illustrated in FIG. 7. Each of the graphs G shows the relationship between the amount of fog and the objective examination result of the eye characteristics measured over time. Thereby, the examinee can compare the graphs G for the left and right subject eye E and determine whether the examinee has anisometropia (unequal vision) or not.

The ophthalmologic apparatus of the present disclosure has been described with reference to the first embodiment. However, the specific configuration of the present disclosure is not limited to the first embodiment. Changes and additions in design should be allowed as long as they do not deviate from the gist of the inventions recited in the claims.

In the first embodiment, the ophthalmologic apparatus 1 of the first embodiment is the binocular open-field type ophthalmologic apparatus that objectively measures the eye characteristics of the left and right subject eye E. However, the ophthalmologic apparatus of the present disclosure is not limited to the ophthalmologic apparatus 1 of the first embodiment and may be a monocular type ophthalmologic apparatus that individually measures the eye characteristics of each eye. Specifically, the ophthalmologic apparatus of the present disclosure may include an objective measurement optical system that objectively measures the eye characteristics of the left subject eye E and the eye characteristics of the right subject eye E one by one.

The left measurement optical system 25L and the right measurement optical system 25R in the ophthalmologic apparatus 1 of the first embodiment includes at least the optotype projection system 42 (subjective measurement optical system 44), the refractive power measurement system 43, and the kerato-system 47. That is, in the first embodiment, the ophthalmologic apparatus 1 has a multi-function that performs the subjective refraction examination as well as the auto-refraction and kerato measurement (auto ref/kerato measurement) under the binocular vision with a single apparatus. However, the ophthalmologic apparatus 1 of the present disclosure is not limited to the above configuration and may be an apparatus that can measure only the refractive power of the subject eye E, for example. In this case, it is preferable for such an ophthalmologic apparatus to include a transmitter that transmits information to at least one second ophthalmologic apparatus (i.e., another ophthalmologic apparatus) that includes a measurement optical system that measures the eye characteristics.

In the case of the ophthalmologic apparatus including the transmitter, the objective examination result of the eye characteristics measured over time can be transmitted by the transmitter to the second ophthalmologic apparatus for setting the measurement condition of the measurement optical system of the second ophthalmologic apparatus. Thereby, the second ophthalmologic apparatus can use the objective examination result, during the fogging, obtained by the ophthalmologic apparatus 1 for the setting of the second ophthalmologic apparatus. That is, the controller 40 including the transmitter can link the ophthalmologic apparatus 1 of the first embodiment with the second ophthalmologic apparatus or apparatuses.

Also, in the first embodiment, the presentation position of the fixation target is changed in the direction to gradually increase the amount of fog and the eye characteristics of the subject eye E are objectively measured at each increase. However, the manner of changing the presentation position of the fixation target and the timing of the objective measurement of the eye characteristics are not limited to the above. For example, while changing the presentation position of the fixation target in a stepless manner in the direction to increase the amount of fog, and the controller 40 may continuously perform the objective measurement of the eye characteristics of the subject eye E during the change in the positions of the fixation target. In this case, the objective examination can be continuously performed in the stepless manner (i.e., continuously) changing the presentation position of the fixation target, and accordingly, the amount of fog that relieves the accommodation of the subject eye E can be accurately understood. Specifically, the objective measurement of the eye characteristics over time includes performing the objective examinations of the eye characteristics a plurality of times while applying the fog to the subject eye E and performing the objective examination of the eye characteristics for a certain period of time (continuously) while applying the fog to the subject eye E.

Also, in the first embodiment, the objective examination is performed in the main measurement (Step S3). However, in the main measurement, the subjective examination may be performed using the subjective measurement optical system 44 after the objective examination. In this case, before the subjective examination, the settings of the subjective measurement optical system 44 may be adjusted in accordance with the objective examination result of the eye characteristics measured over time during the fogging control.

Also, in the first embodiment, it is determined whether or not the objective examination result has converged provided that the amount of fog has reached "the prescribed amount of fog". However, the controller 40 may determine whether or not the objective examination result has converged even when the amount of fog has not reached "the prescribed amount of fog" and terminate the fogging control (determination not to continue changing presentation position of fixation target) at the time of the convergence of the objective examination result to perform the main measurement. In other words, the determination of whether or not the amount of fog has reached "the prescribed amount of fog" (Step S204 in FIG. 4) may not necessarily be performed.

The controller 40 may move the fixation target such that the amount of fog reaches the predetermined amount of fog set in advance and then perform the objective examination of the subject eye E to determine whether or not the objective examination result varies.

Further, in the ophthalmologic apparatus 1 of the first embodiment, the relationship between the amount of fog and the objective examination result is shown in the graph each time the eye characteristics of the subject eye E are objectively measured. However, the graphs may be displayed collectively at any time, for example, when the fogging control is finished (objective examination result has converged) or when the examination such as the main measurement is completed. As illustrated in FIG. 7, the graph G may be displayed on the display 31 in a pop-up manner or displayed on full-screen on the display 31.

Also, the controller 40 performs the objective examination of the subject eye at high speed (e.g., 30 Hz) while changing the presentation position of the fixation target at a constant rate until the amount of fog increases by a predetermined amount and performs the frequency analysis of the objective examination result. Then, it may be determined that "the objective examination result" has converged by identifying the relief of accommodative microfluctuations based on the number of frequency components related to the accommodative microfluctuations of the subject eye E.

In the case where the objective examination result varies in the negative direction (near vision direction), it is conceivable that the subject eye E may have been accommodated regardless of the fixation target. Accordingly, the controller 40 may return the presentation position of the fixation target so that the amount of fog becomes the amount of fog before the objective examination result changes in the negative direction. Then, the controller 40 may present the fixation target at the returned position and apply the fog again to start the main measurement.

Further, in the case where the convergence of the objective examination result is known before the amount of fog has reached "the prescribed amount of fog", the controller 40 returns the presentation position of the fixation target so that the amount of fog becomes the amount of fog at the time of the convergence of the objective examination result before the amount of fog has reached "the prescribed amount of fog". Then, the controller 40 may present the fixation target at the returned position and apply the fog to the subject eye to start the main measurement.

An upper limit (e.g., +3.0D) may be set for the amount of fog. Then, the controller 40 may terminate the fogging control when the amount of fog has reached the upper limit even if the objective examination result has not converged. In this case, the controller 40 notifies the examiner or the like that the tension of the subject eye E has not been relaxed or relieved in addition to the tension tendency of the subject eye E in Step S206. In the case where the tension of the subject eye E has not been relaxed or relieved, the controller 40 may notify the tension tendency and tension state of the subject eye E. Note that "the tension state of the subject eye E" is information that indicates whether or not the tension of the subject eye E is released or relieved. Also, in the first embodiment, the controller 40 does not notify "the tension state of the subject eye E" when the tension of the subject eye E has been relaxed or relieved. In other words, the controller 40 does not notify that the tension of the subject eye E has been relaxed or relieved when the tension of the subject eye E has been relaxed or relieved. However, the controller 40 may notify "the tension state of the subject eye E" regardless of whether or not the tension of the subject eye E has been relaxed or relieved.

Further, in the first embodiment, the controller 40 notifies "the tension tendency of the subject eye E", and "the tension state of the subject eye E" if the tension of the subject eye E has not been relaxed. However, the controller 40 may not notify "the tension tendency of the subject eye E" but may notify only "the tension state of the subject eye E". In other words, the controller 40 may notify only whether the tension of the subject eye E has been relaxed or not. Also, the controller 40 may not necessarily notify "the tension tendency of the subject eye E" and "the tension state of the subject eye E".

What is claimed is:

1. An ophthalmologic apparatus comprising:
an objective measurement optical system that is configured to objectively measure eye characteristics of a subject eye;
an optotype projection system that is configured to present a fixation target to the subject eye at a predetermined presentation position and apply fog to the subject eye; and
a controller that is configured to control the objective measurement optical system and the optotype projection system;
wherein the controller is further configured to preliminarily objectively measure the eye characteristics over time by changing a presentation position of the presented fixation target from the predetermined presentation position in a direction to increase an amount of fog,
wherein the controller presumes that a tension tendency of the subject eye is prone to be tension, meaning that fogging is insufficient and the degree of relief is relatively low, so reaccommodation is likely to occur, in the event that an amount of fluctuation of the objective measurement result from the beginning of the fogging is equal to or greater than a first predetermined amount, or in the event that the sum of the amount of fluctuation in the objective measurement results each time the fixation target position is changed is equal to or greater than a second predetermined amount,
wherein the controller presumes that the tension tendency of the subject eye is not prone to be tension, meaning that tension is sufficiently relieved and reaccommodation is not likely to occur, in the event that the amount of fluctuation of the objective measurement result from the beginning of the fogging is equal to or less than the first predetermined amount, or in the event that the sum of the amount of fluctuation in the objective measurement results each time the fixation target position is changed is equal to or less than the second predetermined amount, and
wherein the controller is further configured to output a notification of at least one of tendency of tension of the subject eye or a state of tension of the subject eye in accordance with the preliminary objective measurement result of the eye characteristics measured over time, wherein the notification is output at an end of the preliminary objective measurement of the eye characteristics over time and before a main measurement of the eye characteristics.

2. The ophthalmologic apparatus according to claim 1, wherein the controller is further configured to set an amount of fog to be increased when changing the presentation position of the fixation target in accordance with an objective measurement result of the eye characteristics measured over time.

3. The ophthalmologic apparatus according to claim 1, wherein the controller is further configured to change the presentation position of the fixation target and determine whether or not to continue applying the fog to the subject eye in accordance with an objective measurement result of the eye characteristics measured over time.

4. The ophthalmologic apparatus according to claim 3, wherein the controller is further configured to
finish changing the presentation position of the fixation target when fluctuation of the objective measurement result has converged to a predetermined range; and
change the presentation position of the fixation target in a direction to increase the amount of fog and continue applying the fog to the subject eye when the fluctuation of the objective measurement result has not converged to the predetermined range.

5. The ophthalmologic apparatus according to claim 1, wherein the controller is further configured to show, in a graph, a relationship between the amount of fog when presenting the fixation target and an objective measurement result of the eye characteristics measured over time.

6. The ophthalmologic apparatus according to claim 1, further comprising a subjective measurement optical system that is configured to subjectively measure eye characteristics of a subject eye; and
wherein the controller is further configured to adjust settings of the subjective measurement optical system in accordance with an objective measurement result of the eye characteristics measured over time, and measure the eye characteristics by the subjective measurement optical system.

7. The ophthalmologic apparatus according to claim 1, wherein the objective measurement optical system comprises:
a left-eye objective measurement system that is configured to objectively measure the eye characteristics of a left subject eye; and
a right-eye objective measurement system that is configured to objectively measure the eye characteristics of a right subject eye.

8. The ophthalmologic apparatus according to claim 7, wherein the objective measurement optical system is configured to objectively measure the eye characteristics of the left subject eye and the eye characteristics of the right subject eye one by one.

9. The ophthalmologic apparatus according to claim 1, further comprising a transmitter that is configured to transmit information to a second ophthalmologic apparatus, the second ophthalmologic apparatus comprising a subjective measurement optical system that is configured to subjectively measure the eye characteristics of the subject eye; and wherein the controller is further configured to transmit an objective measurement result of the eye characteristics measured over time to the second ophthalmologic apparatus via the transmitter for use in setting measurement conditions of the subjective measurement optical system of the second ophthalmologic apparatus.

10. The ophthalmologic apparatus according to claim 1, wherein the controller is configured to perform fogging control, and the fogging control is performed between the preliminary measurement and the main measurement.

11. The ophthalmologic apparatus according to claim 10, wherein the preliminary measurement corresponds to a step of focusing the subject eye on a fogging start position, and the main measurement is a step of measuring predetermined eye characteristics.

12. The ophthalmologic apparatus according to claim 1, wherein the change in the presentation position of the fixation target and the objective measurement associated with the change are repeated until the amount of fog reaches a prescribed amount of fog set in advance.

13. A non-transitory computer-readable storage medium storing a program that, when executed by a processor, causes the processor to:

control an ophthalmologic apparatus comprising:

an objective measurement optical system that is configured to objectively measure eye characteristics of a subject eye;

an optotype projection system that is configured to present a fixation target to the subject eye at a predetermined presentation position and apply fog to the subject eye; and a controller that is configured to control the objective measurement optical system and the optotype projection system;

preliminarily objectively measure the eye characteristics over time by changing a presentation position of the presented fixation target from the predetermined presentation position in a direction to increase an amount of fog;

presume that a tension tendency of the subject eye is prone to be tension, meaning that fogging is insufficient and the degree of relief is relatively low, so reaccommodation is likely to occur, in the event that an amount of fluctuation of the objective measurement result from the beginning of the fogging is equal to or greater than a first predetermined amount, or in the event that the sum of the amount of fluctuation in the objective measurement results each time the fixation target position is changed is equal to or greater than a second predetermined amount;

presume that the tension tendency of the subject eye is not prone to be tension, meaning that tension is sufficiently relieved and reaccommodation is not likely to occur, in the event that the amount of fluctuation of the objective measurement result from the beginning of the fogging is equal to or less than the first predetermined amount, or in the event that the sum of the amount of fluctuation in the objective measurement results each time the fixation target position is changed is equal to or less than the second predetermined amount; and output a notification of at least one of tendency of tension of the subject eye or a state of tension of the subject eye in accordance with the preliminary objective measurement result of the eye characteristics measured over time, wherein the notification is output at an end of the preliminary objective measurement of the eye characteristics over time and before a main measurement of the eye characteristics.

14. The non-transitory computer-readable storage medium according to claim 13, wherein the program, when executed by the processor, further causes the processor to set an amount of fog to be increased when changing the presentation position of the fixation target in accordance with an objective measurement result of the eye characteristics measured over time.

15. The non-transitory computer-readable storage medium according to claim 13, wherein the program, when executed by the processor, further causes the processor to change the presentation position of the fixation target and determine whether or not to continue applying the fog to the subject eye in accordance with an objective measurement result of the eye characteristics measured over time.

16. The non-transitory computer-readable storage medium according to claim 15, wherein the program, when executed by the processor, further causes the processor to finish changing the presentation position of the fixation target when fluctuation of the objective measurement result has converged to a predetermined range; and change the presentation position of the fixation target in a direction to increase the amount of fog and continue applying the fog to the subject eye when the fluctuation of the objective measurement result has not converged to the predetermined range.

17. The non-transitory computer-readable storage medium according to claim 13, wherein the program, when executed by the processor, further causes the processor to show, in a graph, a relationship between the amount of fog when presenting the fixation target and an objective measurement result of the eye characteristics measured over time.

18. The non-transitory computer-readable storage medium according to claim 13, wherein the ophthalmologic apparatus further comprises a subjective measurement optical system that is configured to subjectively measure eye characteristics of a subject eye, and wherein the program, when executed by the processor, further causes the processor to adjust settings of the subjective measurement optical system in accordance with an objective measurement result of the eye characteristics measured over time, and measure the eye characteristics by the subjective measurement optical system.

19. The non-transitory computer-readable storage medium according to claim 13, wherein the objective measurement optical system comprises:

a left-eye objective measurement system that is configured to objectively measure the eye characteristics of a left subject eye; and a right-eye objective measurement system that is configured to objectively measure the eye characteristics of a right subject eye.

20. The non-transitory computer-readable storage medium according to claim 19, wherein the objective measurement optical system is configured to objectively measure the eye characteristics of the left subject eye and the eye characteristics of the right subject eye one by one.

21. The non-transitory computer-readable storage medium according to claim 13, wherein the ophthalmologic apparatus further comprises a transmitter that is configured to transmit information to a second ophthalmologic apparatus, the second ophthalmologic apparatus comprising a subjective measurement optical system that is configured to subjectively measure the eye characteristics of the subject eye; and wherein the program, when executed by the processor, further causes the processor to transmit an objective measurement result of the eye characteristics measured over time to the second ophthalmologic apparatus via the transmitter for use in setting measurement conditions of the subjective measurement optical system of the second ophthalmologic apparatus.

22. The non-transitory computer-readable storage medium according to claim 13, wherein the program, when executed by the processor, further causes the processor to perform fogging control, and the fogging control is performed between the preliminary measurement and the main measurement.

23. The non-transitory computer-readable storage medium according to claim 22, wherein the preliminary measurement corresponds to focusing the subject eye on a fogging start position, and the main measurement corresponds to measuring predetermined eye characteristics.

24. The non-transitory computer-readable storage medium according to claim 13, wherein the change in the presentation position of the fixation target and the objective measurement associated with the change are repeated until the amount of fog reaches a prescribed amount of fog set in advance.

\*　\*　\*　\*　\*